US008956276B2

(12) United States Patent
Young et al.

(10) Patent No.: US 8,956,276 B2
(45) Date of Patent: Feb. 17, 2015

(54) IMPLANT FOR PELVIC ORGAN PROLAPSE REPAIR

(75) Inventors: Robert Young, Bogart, GA (US); Walter Freitag, Atlanta, GA (US); Doug Evans, Snellville, GA (US)

(73) Assignee: C.R. Bard, Inc., Covington, GA (US)

( * ) Notice: Subject to any disclaimer, the term of this patent is extended or adjusted under 35 U.S.C. 154(b) by 448 days.

(21) Appl. No.: 13/147,486

(22) PCT Filed: Dec. 21, 2009

(86) PCT No.: PCT/US2009/069074
§ 371 (c)(1),
(2), (4) Date: Jan. 19, 2012

(87) PCT Pub. No.: WO2010/087923
PCT Pub. Date: Aug. 5, 2010

(65) Prior Publication Data
US 2012/0108894 A1      May 3, 2012

Related U.S. Application Data

(60) Provisional application No. 61/149,073, filed on Feb. 2, 2009.

(51) Int. Cl.
*A61F 2/00*        (2006.01)
*A61F 13/00*      (2006.01)

(52) U.S. Cl.
CPC .................................. *A61F 2/0045* (2013.01)
USPC ................. 600/37; 600/29; 600/30; 606/151; 128/897; 128/898; 128/899

(58) Field of Classification Search
USPC .......... 600/29, 30, 37; 606/151; 128/897–899
See application file for complete search history.

(56) References Cited

U.S. PATENT DOCUMENTS

| | | | |
|---|---|---|---|
| 6,884,212 | B2 | 4/2005 | Thierfelder et al. |
| 2003/0220538 | A1 | 11/2003 | Jacquetin |
| 2006/0229493 | A1 * | 10/2006 | Weiser et al. ................... 600/37 |
| 2007/0123915 | A1 | 5/2007 | Kammerer et al. |
| 2008/0177132 | A1 * | 7/2008 | Alinsod et al. .................. 600/37 |

OTHER PUBLICATIONS

International Search Report and Written Opinion dated Apr. 23, 2010, for PCT/US2009/069074.

* cited by examiner

*Primary Examiner* — Christine Matthews
*Assistant Examiner* — Sunita Reddy
(74) *Attorney, Agent, or Firm* — Knobbe Martens Olson & Bear LLP (57) ABSTRACT

A medical article is used to repair prolapses of various pelvic organs including vaginal vault prolapse. The medical article can include a first flap comprising a dual density mesh formed of a first and second filament, a second flap comprising a single density mesh formed of the first filament, and a third flap comprising a single density mesh formed of the second filament. The first, second, and third flap can share a common intersection that can form an arc. The medical article can be formed by knitting a uniform piece of mesh and the arc can be configured to conform to a surface of a pelvic organ. Methods of manufacturing and methods of using the medical article are also disclosed.

17 Claims, 12 Drawing Sheets

IMPLANT FOR PELVIC ORGAN PROLAPSE REPAIR

CROSS-REFERENCE TO RELATED APPLICATIONS

This application is the National Stage of International Application No. PCT/US2009/069074, filed on Dec. 21, 2009, entitled "IMPLANT FOR PELVIC ORGAN PROLAPSE REPAIR," which claims the benefit of U.S. Provisional Patent Application No. 61/149,073, entitled "IMPLANT FOR PELVIC FLOOR REPAIR" filed Feb. 2, 2009, both of which are hereby expressly incorporated by reference in their entireties.

BACKGROUND OF THE INVENTION

1. Field of the Invention

This invention relates to an implantable medical article. More particularly, the invention relates to an implantable medical article that may be used to treat pelvic organ prolapse disorders, for example, vaginal vault prolapse.

2. Description of the Related Art

Pelvic organ prolapse disorders typically result from weakness in or damage to normal pelvic organ support structures. Pelvic organ prolapse disorders can include cystocele, rectocele, enterocele, uterine vault prolapse, and vaginal vault prolapse. These disorders can result from childbirth, removal of the uterus, connective tissue defects, postmenopausal atrophy, and heavy labor.

Vaginal vault prolapse occurs when the upper portion of the vagina loses its normal shape and sags or bulges down into the vaginal canal or outside of the vagina. It may occur alone or along with prolapse of the bladder (cystocele), urethra (urethrocele), rectum (rectocele), or small bowel (enterocele). Symptoms of vaginal vault prolapse can include: pelvic heaviness; backache; discomfort during intercourse; a mass bulging out of the vagina; incontinence; and/or vaginal bleeding.

Vaginal vault prolapse can be treated surgically with a sacrocolpopexy procedure which includes connecting the vagina with another point within the pelvic cavity, for example, the lower spine, the sacrum, or the ligaments of the pelvis. In some cases, an implantable medical article is used to suspend the vagina within the pelvic cavity. The medical article can be introduced into the pelvic cavity of the patient through the vagina or through an abdominal incision. Various other procedures and treatments are also used to treat vaginal vault prolapse and prolapses of other various pelvic organs.

SUMMARY OF THE INVENTION

The devices and methods of the present invention have several features, no single one of which is solely responsible for its desirable attributes. Without limiting the scope of this invention as expressed by the claims which follow, its more prominent features will now be discussed briefly. After considering this discussion, and particularly after reading the section entitled "Detailed Description of Certain Embodiments" one will understand how the features of this invention provide several advantages over other implantable medical articles.

One aspect of the present invention is an implantable medical article for use in a procedure to repair a pelvic organ prolapse, the medical article having a length along a longitudinal axis. The medical article can include a first flap comprising a dual density polymer mesh, the dual density polymer mesh including a first filament and a second filament, the first flap having a first width, a second flap comprising a single density polymer mesh, the second flap comprising the first filament, the second flap having a second width, and a third flap comprising a single density polymer mesh, the third flap comprising the second filament, the third flap having a third width, wherein the first flap, the second flap, and the third flap form an intersection comprising an arc.

Another aspect of the present invention is an implantable medical article comprising at least three flexible flaps arranged generally in a y-configuration, only two of the at least three flaps having the same density.

Another aspect of the present invention is a method of treating a pelvic organ prolapse of a patient comprising providing the medical article comprising a first flap, a second flap, and a third flap, wherein the first flap, second flap, and third flap form an intersection comprising an arc, introducing the medical article into a pelvic cavity of the patient, positioning the intersection over an apex of a vagina of the patient, attaching the second flap to a first wall of the vagina, attaching the third flap to a second wall of the vagina, the second wall being generally opposite the first wall, and attaching the first flap to an anterior longitudinal ligament overlying a sacral promontory.

Yet another aspect of the present invention is a method of manufacturing a uniform implantable medical article comprising knitting a first portion comprising a dual density mesh, knitting a second portion comprising a single density mesh, and knitting a third portion comprising a single density mesh, wherein the first portion, second portion, and third portion share a common intersection.

Another aspect of the present invention is a method of manufacturing a plurality of implantable medical articles using a double needle bar warp knitting machine. The method includes feeding a first filament into a first needle bar, knitting the first filament into a layer of fabric, feeding a second filament into a second needle bar, knitting the second filament into a layer of fabric, exchanging positions of the first needle bar and the second needle bar, and knitting the first filament and second filament together to form a continuous layer of fabric.

BRIEF DESCRIPTION OF THE DRAWINGS

These and other features, aspects, and advantages of the invention disclosed herein are described below with reference to the drawings of preferred embodiments. which are intended to illustrate and not to limit the invention. Additionally, from figure to figure, the same reference numerals have been used to designate the same components of an illustrated embodiment. The following is a brief description of the drawings.

DETAILED DESCRIPTION OF CERTAIN EMBODIMENTS

The following description and the accompanying figures, which describe and show the preferred embodiments, are made to demonstrate several possible configurations that an implantable medical article can take to include various aspects and features of the invention. In some of the figures, an illustrated embodiment is shown in use in a pelvic cavity of a patient. The illustration of the medical article in this context is not intended to limit the disclosed aspects and features of the invention to the specified embodiments or usage only within the pelvic cavity. Those of skill in the art will recognize that the disclosed aspects and features of the invention are not limited to any particular embodiment of an implantable medical article.

Figure 1:
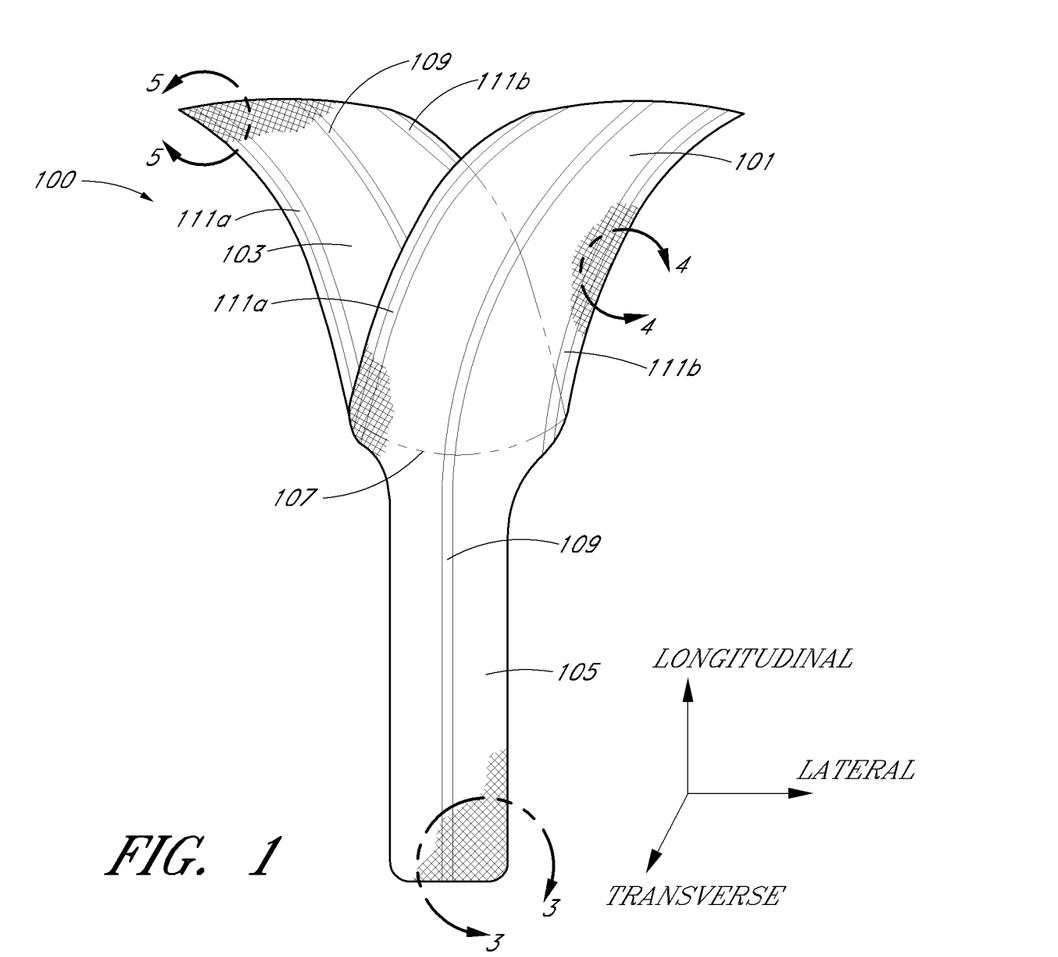
FIG. 1 is a perspective view of an implantable medical article according to one embodiment that has a sacral flap and two engagement flaps.

To assist in the description of these components of the medical article, the following coordinate terms are used (see FIG. 1). Unless defined otherwise, all technical and scientific terms used herein are intended to have the same meaning as is commonly understood by one of ordinary skill in the relevant art.

As used herein, the singular forms "a," "an," and "the" include the plural reference unless the context clearly dictates otherwise. A "longitudinal axis" is generally parallel to a portion of the implantable medical article. A "lateral axis" is normal to the longitudinal axis and parallel to the sacral flap. A "transverse axis" extends normal to both the longitudinal and lateral axes. The "longitudinal direction" refers to a direction substantially parallel to the longitudinal axis; the "lateral direction" refers to a direction substantially parallel to the lateral axis; and the "transverse direction" refers to a direction substantially parallel to the transverse axis.

As used herein, the terms "posterior" "anterior," which are used to describe the present implantable medical article and portions of the patient's anatomy, are used consistently with the description of the exemplary applications. Thus, posterior and anterior are used in reference to the front and back sides of the patient's body. For example, the anterior wall of a vagina is the wall of the vagina that is located nearest the front side of the patient and the posterior wall of the vagina is the wall that is located nearest the back side of the patient. The terms "upper," "lower," "top," "bottom," "underside," "upperside" and the like, which also are used to describe the present medical article, are used in reference to the illustrated orientation of the embodiment and in reference to various portions of the patient's anatomy. For example, the term "upperside" is used to describe the portion of the medical article that is closest to the head of the patient.

Various aspects will now be described with reference to specific forms or embodiments selected for purposes of illustration. It will be appreciated that the spirit and scope of the medical article disclosed herein is not limited to the selected forms. Moreover, it is to be noted that the figures provided herein are not drawn to any particular proportion or scale, and that many variations can be made to the illustrated embodiments. Brief introductions to some of the features, which are common to the described embodiments of the medical articles, are now described. Those of skill in the art will recognize that the disclosed aspects and features shown herein are not limited to any particular form of an implantable medical article, and medical articles that include one or more of the features described herein can be designed for use in a variety of applications.

The forms disclosed herein provide an implantable medical article for use in repairing prolapses of various pelvic organs, for example, vaginal vault prolapse. The medical article is formed of an integral piece of mesh and can be generally y-shaped. That is to say the medical article can be formed of one piece of mesh and can include at least three flaps. The medical article can include a first flap comprising dual density mesh, a second flap comprising single density mesh, and a third flap comprising single density mesh. In another embodiment, the medical article can include two pairs of single density mesh flaps linked together by a piece of dual density mesh. The medical article can also include a dual density mesh flap and two single density mesh flaps that form a cup shape for at least a portion of the length of the flaps. Additional embodiments are also disclosed herein.

In use, the medical article can be used to suspend a pelvic organ at a certain location within the pelvic cavity of a patient. The single density flaps may be coupled or attached to separate portions of a prolapsed pelvic organ. For example, the single density flaps may be sutured to opposite walls of a prolapsed vagina. The dual density flap may then be attached to another point within the pelvic cavity, for example, to the anterior longitudinal ligament at the level of the sacral promontory, to suspend the pelvic organ within the pelvic cavity from the dual density flap point of attachment. The dual density flap may be attached to a point within the pelvic cavity using permanent sutures or another fixation methodology.

The mesh or fabric used to form the medical article can be knit or woven using various knitting methods, for example, by using a double needle bar warp knitting machine or a double needle bar raschel machine. The mesh can be configured to exhibit different elongation characteristics along different directions. For example, the mesh can exhibit limited elongation in the longitudinal direction for stability between the suspended pelvic organ and the other point of attachment while allowing substantial elongation in the lateral direction to allow for pelvic organ distention and movement. Lateral flexibility of the implantable article is important to prevent discomfort in the patient, for example, by allowing the implantable article to expand and contract with a vagina that is sutured to the medical article.

In some of the forms described herein, two or more flaps of the medical article can meet at an intersection. The intersection may be generally curved to conform to the shape of a portion of a pelvic organ, for example, an apex of a vagina. The medical article may be woven as an integral piece of mesh. For example, the dual density flap may be woven using two filaments and each filament may also be used to weave a separate single density flap attached to the dual density flap at the common intersection. This integral design provides stability and uniformity across the medical article. In some embodiments, the medical article can include more than one intersection.

To facilitate a complete understanding of the embodiments disclosed herein, the remainder of the detailed description describes the medical article with reference to the attached figures, wherein like elements among the embodiments are references with like numerals throughout the following description.

Medical Article

Figure 2:
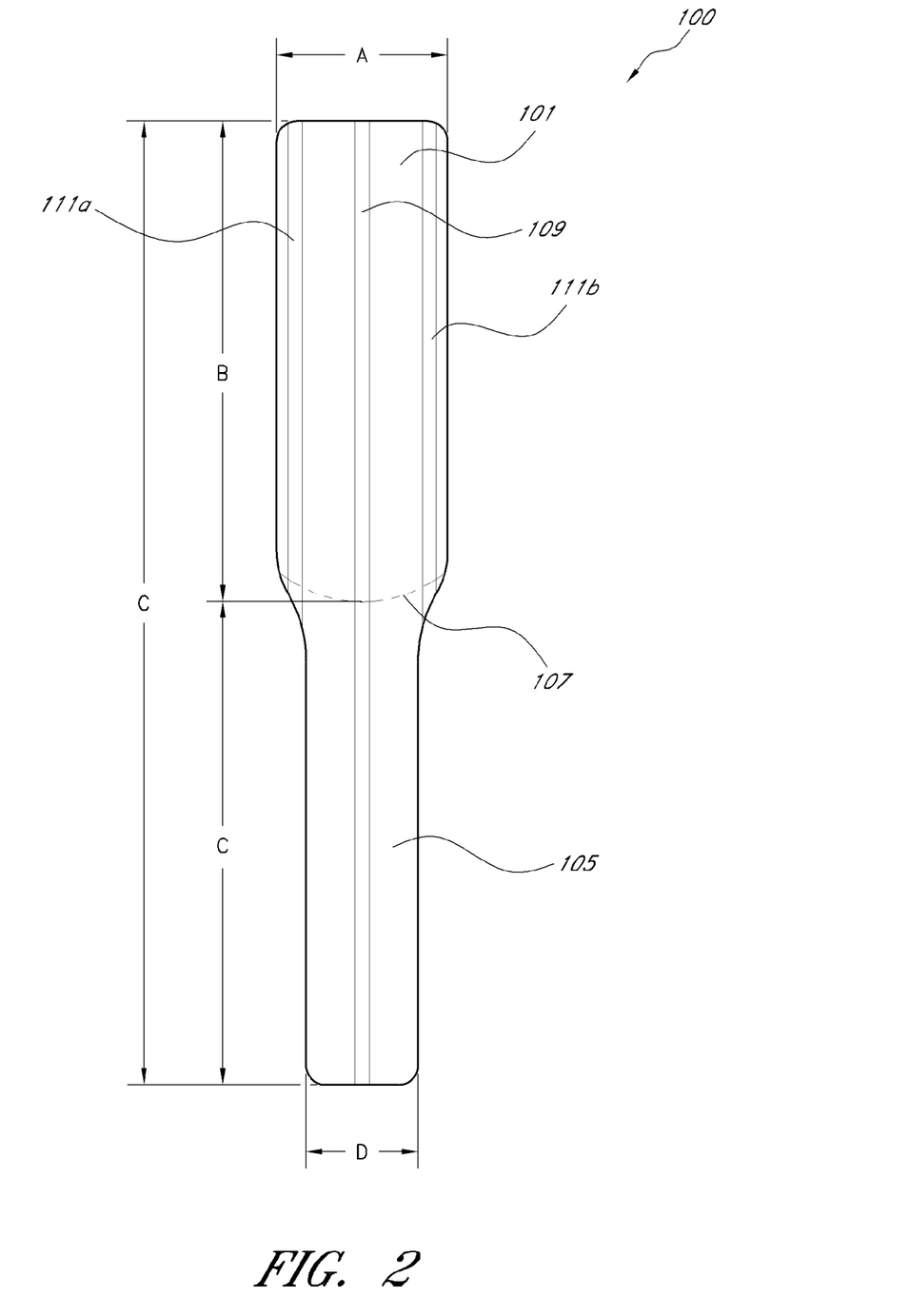
FIG. 2 is a side view of the implantable medical article shown in FIG. 1 with the two engagement flaps folded toward one another.

FIG. 1 is a perspective view of a medical article 100 configured in accordance with an embodiment of the present invention and FIG. 2 is a side view of the medical article 100 of FIG. 1 with the two engagement flaps folded together. As shown in FIG. 1, the illustrated medical article 100 is generally y-shaped and includes three main components: two pelvic organ engagement flaps 101, 103 and a sacral flap 105. The two pelvic organ engagement flaps 101, 103 and the sacral flap 105 meet at a common intersection 107. Intersection 107 may be generally straight or generally arc shaped as shown in FIG. 1. The shape of the intersection 107 may vary depending on the intended application for the medical article 100. For example, the intersection 107 may be arc shaped to generally conform to a portion of a pelvic organ such as an apex of a vagina. In other embodiments, the intersection 107 may not be intended to engage a surface of a pelvic organ and may be differently shaped. The medical article 100 is formed of an integral piece of mesh, for example, a lightweight non-absorbable polypropylene mesh. The mesh may be designed with limited elongation in the longitudinal direction for stability while maintaining substantial elongation in the lateral direction for pelvic organ movement and distention.

FIG. 2 also illustrates a set of dimensions for an exemplary embodiment of the medical article 100 shown with the flaps folded towards each other. Width A is a dimension of pelvic organ engagement flap 101 measured between two sides of the flap 101 in a lateral direction as shown. Length B is a dimension of the pelvic organ engagement flap 101 measured between an end of the flap 101 and the middle of the intersection 107 in a longitudinal direction as shown. Width D is a dimension of sacral flap 105 measured between two sides of the flap 105 in a lateral direction as shown. Length C is a dimension of the sacral flap 105 measured between an end of the flap 105 and the middle of the intersection 107 in a longitudinal direction as shown.

The dimensions of the medical article 100 and flaps 101, 103, 105 can vary depending upon the intended application. For example, the medical article 100 may be designed such that width A is greater than width D so that the sacral flap 105 may fit more easily into a narrow space while flap 101 is substantially wide enough to cover an intended portion of a pelvic organ, for example, a portion of a vaginal wall. The medical article 100 may also be designed so that width A is about the same as width D to allow a healthcare provider to tailor the medical article to fit in an intended application as discussed below. The dimensions of the medical article 100 can also be chosen such that tension is evenly distributed along a curved arc that generally matches the shape of a pelvic organ, for example, the shape of a vagina.

The width of each flap 101, 103, 105 can vary along the longitudinal axis of the medical article 100 or can remain substantially the same for the length of the flap. For example, the width of the sacral flap 105 can increase near the intersection 107. The lengths B and C can also vary depending upon the intended application of the medical article 100. For example, in some applications the medical article 100 can be used to engage a small portion of a pelvic organ and the engagement flap 101 may have a smaller length B to match the portion of the pelvic organ. Similarly, the dimensions of one of the pelvic organ engagement flaps 101, 103 may be different than the dimensions of the other flap. Such configurations allow the engagement flaps 101, 103 to engage asymmetrical portions of pelvic organs. The dimensions of each pelvic organ engagement flap 101, 103 may also be identical and a healthcare provider can trim or otherwise alter the dimensions of one or more flaps as needed.

Length C of the sacral flap 105 may vary according to the distance between a connection point within the pelvic cavity and the pelvic organ to be repaired. For example, a medical article 100 for use in repairing a vaginal vault prolapse may have a longer length C than a medical article for use in repairing a rectocele because the distance between the vagina and the sacrum is greater than the distance between the rectum and the sacrum.

In some embodiments where the medical article 100 is used to repair vaginal vault prolapses, length B of engagement flap 101 ranges from about 80 mm to about 160 mm, length C ranges from about 80 mm to about 160 mm, width A ranges from about 40 mm to about 60 mm, and width D ranges from about 20 mm to about 40 mm. The dimensions may be chosen such that the medical article 100 is large enough to be used with most patients suffering from vaginal vault prolapse. As discussed below, the medical article 100 may be tailored or cut to fit in patients where the medical article 100 is initially too large for its intended application. Accordingly, the medical article 100 may be manufactured to fit the largest of patients.

As shown in FIGS. 1 and 2, the medical article 100 can include a centerline indicator 109 running in a longitudinal direction across the medical article. Each of the flaps 101, 103 can further include at least two lateral indicators 111(a), 111(b) disposed on opposite sides of the centerline indicator 109. The indicators 109, 111(a), 111(b) can be formed from colored thread woven into the mesh or by printing lines on the mesh after it is knitted.

The centerline indicator 109 can be used by a healthcare provider to align the medical article 100 within the pelvic cavity of a patient with respect to a pelvic organ and another point of attachment, for example, with respect to a point on the patient's sacrum. The lateral indicators 111(a), 111(b) can also be used for alignment purposes and to provide the healthcare provider with a reference point for the lateral sides of the engagement flaps 101, 103. For example, if the engagement flaps 101, 103 are to be sutured to portions of a pelvic organ, the sutures are desirably placed at least 1 cm away from the edges of the flaps 101, 103 and the healthcare provider can place the sutures medial to the lateral indicators 111(a), 111(b) to ensure they are placed at a sufficient distance away from the edges. In many cases, pelvic organ prolapse disorders may be repaired laparoscopically and thus, the centerline 109 and lateral indicators 111(a), 111(b) may be useful to a healthcare professional positioning the medical article 100 within a pelvic cavity while viewing the medical article through a laparoscope.

Figure 3:
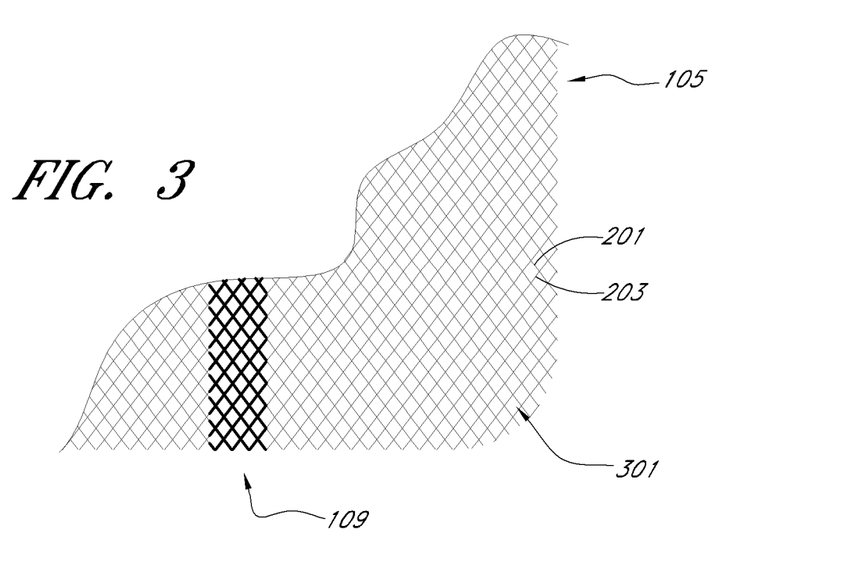
FIG. 3 is a close-up view of the lower right corner of the sacral flap shown in FIG. 1.
Figure 4:
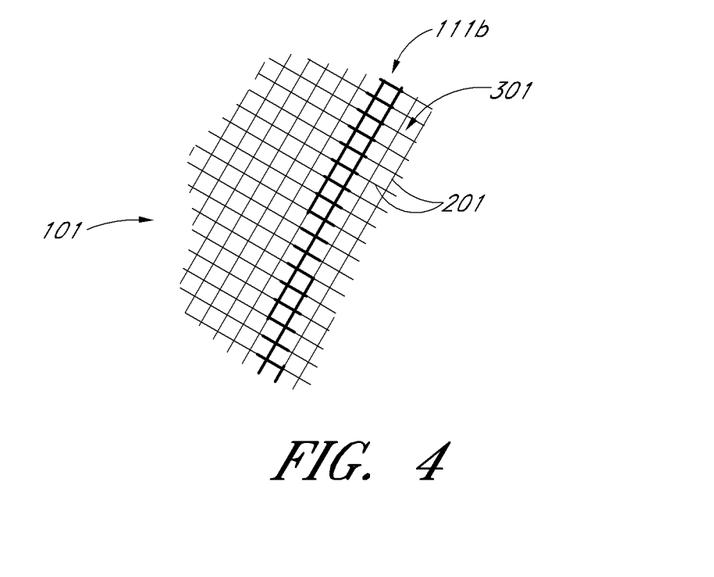
FIG. 4 is a close-up view of a portion of one of the engagement flaps shown in FIG. 1.
Figure 5:
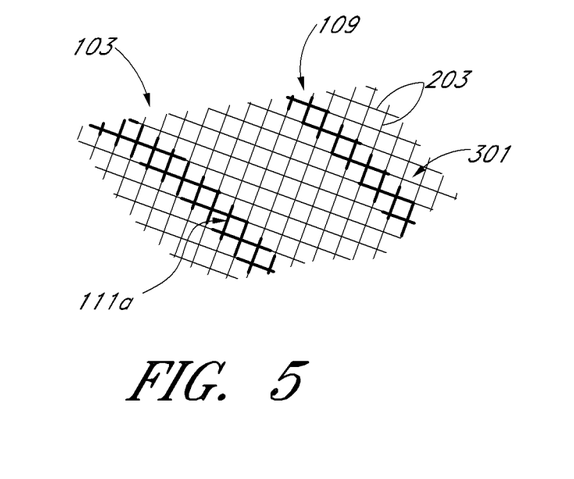
FIG. 5 is a close-up view of a portion of the other engagement flap shown in FIG. 1.

FIGS. 3-5 show close-up views of different portions of the medical article 100. FIG. 3 shows a close-up view of a portion of the sacral flap 105. The sacral flap 105 is formed by knitting at least two filaments 201, 203 to form a dual density mesh. The sacral flap 105 may be knit or woven using a double needle bar warp knitting machine, a double needle bar raschel machine, a similar knitting machine, or by other known knitting methods. The knitting method selected can allow a healthcare provider to trim a portion of the flap 105 without the flap unraveling.

Each separate filament 201, 203 may comprise a lightweight non-absorbable polypropylene or similar material. Of course each filament 201, 203 need not comprise the same material and may instead comprise different materials.

Pores 301 are formed between the filaments 201, 203. The sizes and shapes of the pores 301 can vary depending on the materials chosen for each filament 201, 203 and the knitting method used. For example, the pores may each have an area of between about 1.5 mm$^2$ and about 2.5 mm$^2$. Similarly, the density of the sacral flap 105 can vary depending on the materials chosen for each filament 201, 203 and how the filaments are knit together. In one embodiment, the sacral flap 105 has a thickness of about 0.40 mm and a density of about 35.55 g/m$^2$.

As mentioned above, the knitting method used may be designed to form an integral mesh that exhibits limited elongation in the longitudinal direction while allowing substantial elongation in the lateral direction. These elongation characteristics allow a pelvic organ to flex or move in one direction while holding the pelvic organ stable in another direction. For example, a medical article 100 may be used to suspend a patient's vagina from a point inside the pelvic cavity near the sacrum such as a point on the anterior longitudinal ligament at the level of the sacral promontory. The limited elongation of the medical article 100 in the longitudinal direction acts to maintain the suspension of the vagina in a general location within the cavity and the substantial lateral elongation of the medical article allows the vagina to expand laterally without discomfort, for example, during intercourse.

FIGS. 4 and 5 illustrate close-up views of portions of the engagement flaps 101, 103, respectively. FIG. 4 shows a close-up view of a portion of engagement flap 101 that is formed of a mesh woven from filament 201. FIG. 5 shows a close-up view of a portion of engagement flap 103 that is formed of a mesh woven from filament 203. As shown, engagement flaps 101, 103 are each formed of a single-density knit with a single filament.

In some embodiments the engagement flaps 101, 103 are substantially identical to one another and are manufactured from the same filament material. The sizes and shapes of the pores 301 in the engagement flaps 101, 103 can vary from the pores in the sacral flap 105 when the engagement flaps 101, 103 are knit using a single filament instead of two filaments. For example, the pores 301 in the engagement flaps may each have an area of between about 3 mm$^2$ and about 4.5 mm$^2$. When the engagement flaps 101, 103 comprise single density mesh and the sacral flap 105 comprises double density mesh, the densities of the flaps 101, 103 are about half of the density of the sacral flap 105. For example, each engagement flap 101, 103 may have a density of about 17.67 g/m$^2$ and a thickness of about 0.29 mm. The lower density of the engagement flaps 101, 103 allows the flaps to softly engage portions of a pelvic organ while the medical article 100 stably suspends the pelvic organ within the pelvic cavity.

As discussed above, the medical article 100 can be manufactured using various knitting methods. In one method of manufacturing the medical article 100, two sets of individual filaments or fibers are fed into two separate needle bars; each needle being configured to knit an independent layer of substantially identical fabric. After a certain length of fabric has been knit, the needle bar positions are swapped resulting in the two sets of individual filaments being woven together creating a single continuous sheet of dual density mesh. By alternating between the two needle bar positions, the knitting machine alternates between simultaneously knitting two separate layers of single density mesh and knitting a single layer of dual density mesh to produce one uniform piece of mesh that is formed of two separate filaments 201, 203.

Operation

An exemplary process for treating a patient suffering from a pelvic organ prolapse with the medical article 100 described above will now be described with reference to FIGS. 6A and 6B. Two methods of using the medical article 100 will be described in the context of repairing a vaginal vault prolapse. However, as stated above, the aspects and features of the operational method and use of the present medical article 100 are not limited to this particular application. For example, the medical article 100 may also be used to repair prolapse of the bladder or rectum.

In one method, a healthcare provider begins by preparing the patient anatomy for attachment of the medical article 100 to opposite walls of the vagina and the anterior longitudinal ligament overlying the sacral promontory. The medical article 100 is desirably attached to the anterior and posterior walls of the vagina, but the healthcare provider can attach the medical article to any two outer surfaces on the vagina. Similarly, the medical article 100 is also desirably attached to the anterior longitudinal ligament overlying the sacral promontory but the healthcare provider can attach to medical article to other points within the pelvic cavity including the sacrum. The healthcare provider can prepare the patient anatomy using open surgical techniques or laparoscopic methods.

After preparing the patient anatomy, the healthcare provider can designate one of the pelvic organ engagement flaps 101, 103 as the "anterior flap" and the other of the pelvic organ engagement flaps as the "posterior flap." In the illustrated embodiment, pelvic organ engagement flap 101 is designated as the anterior flap and the other pelvic organ engagement flap 103 is designated as the posterior flap. The healthcare provider can measure the length of the anterior wall of the vagina that is to be attached to the anterior flap and the length of the posterior wall of the vagina that is to be attached to the posterior flap. If necessary, the healthcare provider trims the anterior flap to match the measured portion of the anterior wall and trims the posterior flap to match the measured portion of the posterior wall. In some circumstances, the anterior flap and posterior flap may be appropriately sized for placement within the patient so as to not require trimming.

The healthcare provider may also determine whether or not the widths of the anterior and posterior flaps need to be trimmed to match the widths of the anterior and posterior walls of the vagina. In most cases, the size of the vagina will be large enough such that the posterior and anterior flaps do not meet when positioned on opposite walls of the vagina. In cases where the patient has a vagina with a smaller than average girth, the widths of the anterior flaps and the posterior flaps may be trimmed using the lateral indicators 111(a), 111(b) as points of reference.

Figure 6A:
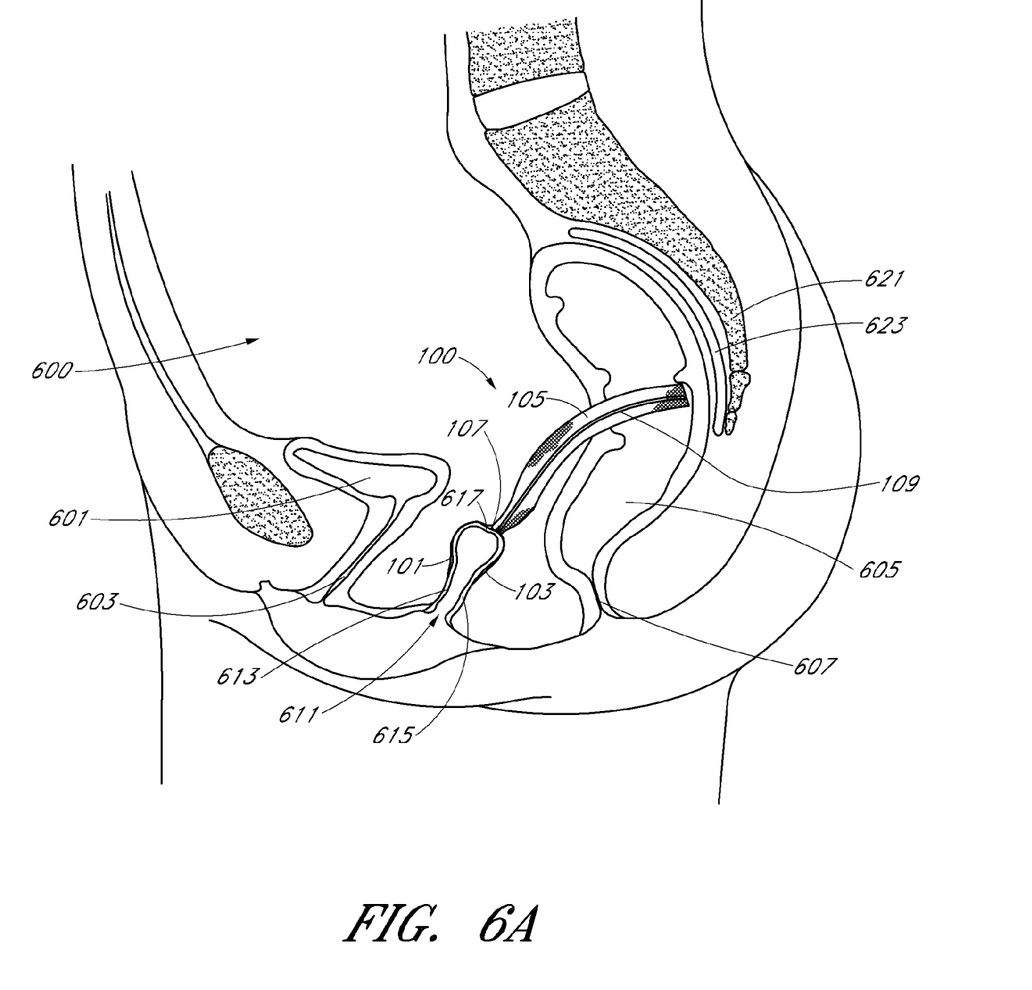
FIG. 6A is a side view of the implantable medical article from FIG. 1 positioned within a pelvic cavity of a patient suffering from vaginal vault prolapse prior to securement of its distal end to the anterior longitudinal ligament.

Turning now to FIG. 6A, a medical article 100 is shown positioned within a pelvic cavity 600. The pelvic cavity 600 includes a bladder 601, a urethra 603, a vagina 611, an anterior wall of the vagina 613, a posterior wall of the vagina 615, an apex of the vagina 617, a small intestine 605, a rectum 607, a sacrum 621, and a longitudinal ligament at the level of the sacral promontory 623. If trimming is required, the healthcare provider may or may not trim the medical article 100 prior to placement within the patient. The healthcare provider introduces the medical article 100 into the pelvic cavity 600 of the patient. The healthcare provider may orient the anterior flap 101 with respect to the anterior wall 613 and the posterior flap 103 with respect to the posterior wall 615 and position the medical article such that the intersection 107 abuts the apex of the vagina 617. The medical professional may use the centerline indicator 109 as a reference to position the medical article with respect to the vagina 611 and the sacral promontory 623.

The healthcare provider may permanently attach the anterior flap 101 to the anterior wall 613 of the vagina and permanently attach the posterior flap 103 to the posterior wall 615 of the vagina. The healthcare provider may use any suitable method of attachment including sutures. For example, sutures can be placed at least 1 cm away from any mesh edge. One or more sutures may be employed. For example, the healthcare provider may use 4 permanent sutures to attach the flaps 101, 103 to their respective vaginal walls.

Figure 6B:
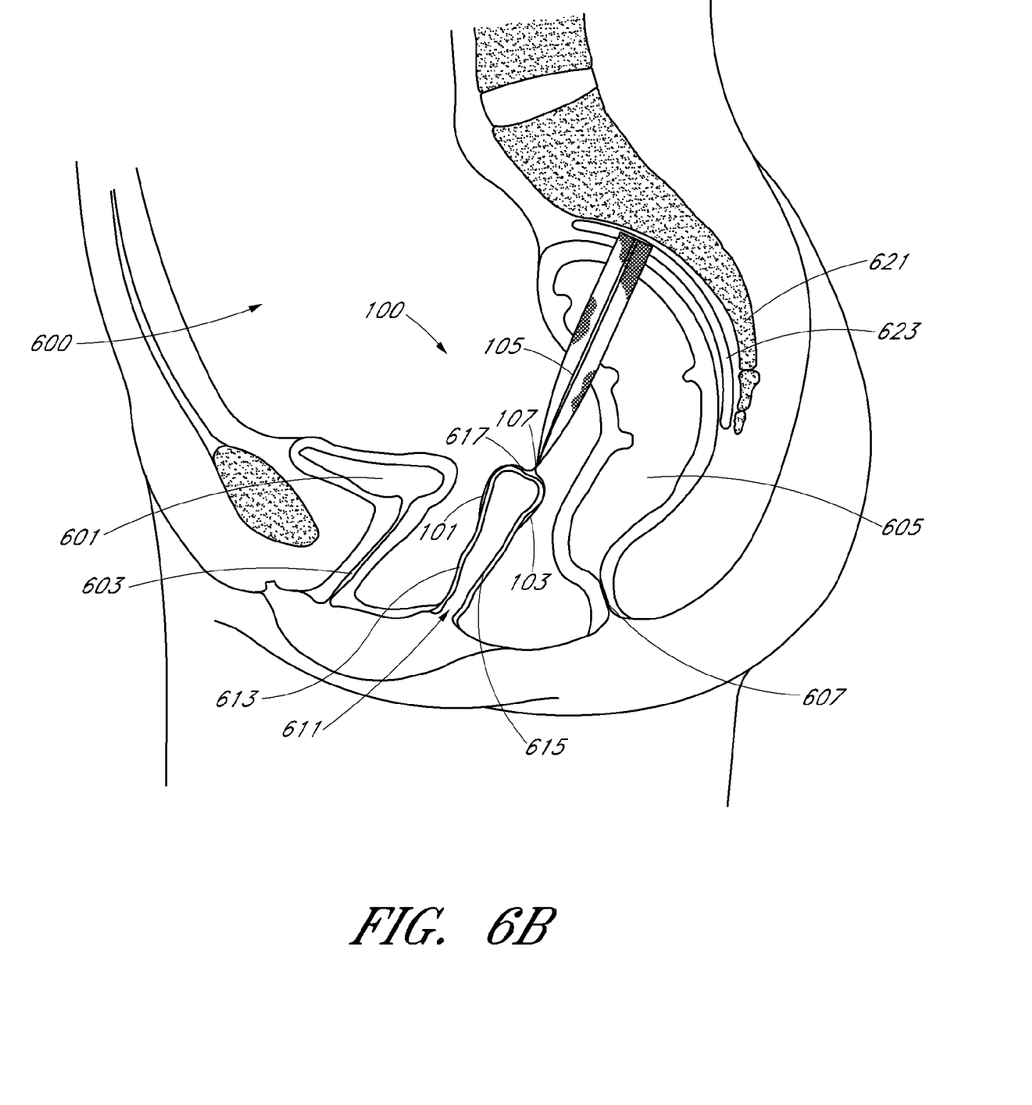
FIG. 6B is a side view of the implantable medical article of FIG. 6A secured to the vagina and the anterior longitudinal ligament of the patient in order to suspend the vagina within the pelvic cavity to treat the vaginal vault prolapse.

Turning now to FIG. 6B, the healthcare provider can proceed to attach the sacral flap 105 to the anterior longitudinal ligament 623 at a point overlying the sacrum 621, for example, at the sacral promontory, before or after attaching the pelvic organ engagement flaps 101, 103 to the vagina.

The healthcare professional should ensure appropriate tension in the sacral flap 105 such that the vagina 611 is lifted into the pelvic cavity 600 from its prolapsed position and suspended in a general area. The healthcare provider may attach the sacral flap 105 to the anterior longitudinal ligament 623 using various fixation techniques including permanent sutures and/or screws. For example, the healthcare provider can use two permanent sutures to attach the sacral flap 105 to the anterior longitudinal ligament 623. Any excess portion of the sacral flap 105 near the points of attachment to the anterior longitudinal ligament 623 may then be trimmed off and removed from the pelvic cavity 600. After the medical article 100 is properly implanted within the patient, the medical article 100 may be reperitonealized using known techniques.

In a second method, a healthcare provider introduces the medical article 100 into the pelvic cavity 600 of a patient using laparoscopic or open surgical techniques. The healthcare provider then aligns pelvic organ engagement flaps 101 with the anterior wall of the vagina 613 and pelvic organ engagement flap 103 with the posterior wall of the vagina 615. The healthcare provider then determines if the pelvic organ engagement flaps 101, 103 need to be trimmed down to match the anterior wall 613 and posterior wall 615. If so, the healthcare provider uses the lateral indicators 111(a), 111(b) as points of reference and trims the medical article 100 while it is inside the patient and removes the excess portions from the pelvic cavity. The healthcare provider can then proceed with attaching the medical article 100 to the patient as set forth above in the first method. The methods of vaginal vault prolapse repair disclosed herein may be adapted to repair other prolapsed pelvic organs, for example, bladders, rectums, uteruses, and small intestines.

Additional Embodiments

Figure 7:
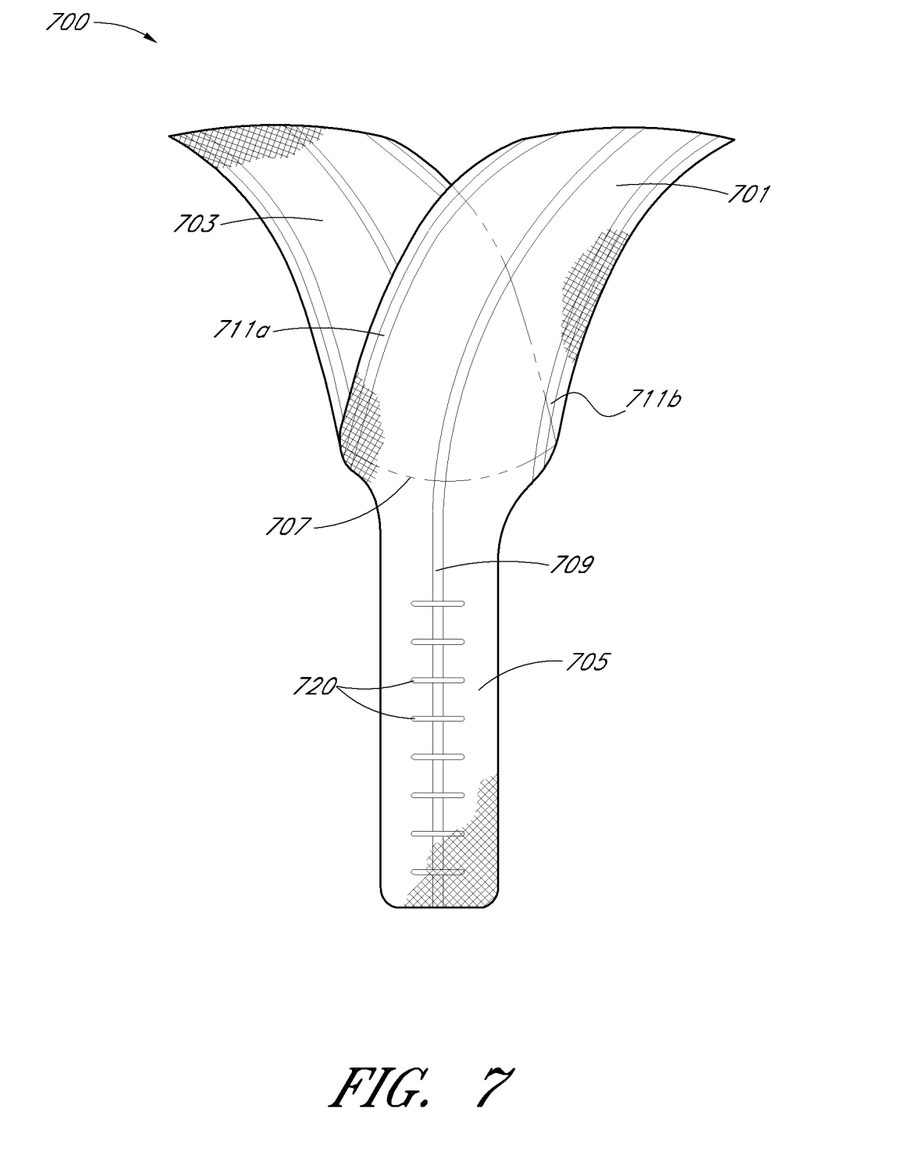
FIG. 7 is a perspective view of an implantable medical article according to another embodiment that includes hash marks.

FIGS. 7-12 illustrate additional embodiments of implantable medical articles that can be used to repair various pelvic organ prolapse disorders. FIG. 7 is a perspective view of an embodiment of an implantable medical article 700. The medical article 700 is generally y-shaped and includes three main components: two pelvic organ engagement flaps 701, 703 and a sacral flap 705. The two pelvic organ engagement flaps 701, 703 meet at a common intersection 707. Intersection 707 can be generally straight or generally arc shaped as shown in FIG. 7. The medical article 700 can also include a centerline indicator 709 and lateral indicators 711a, 711b.

The hash marks 720 can be disposed across and generally perpendicular to the centerline indicator 709. The hash marks 720 can be spaced about evenly from one another to provide a visual measuring reference for a healthcare provider. For example, a healthcare provider can introduce the medical article 700 into a pelvic cavity of a patient and laparoscopically determine that the sacral flap 705 should be trimmed with reference to a selected hash mark 720 to remove an excess portion of the flap 705. The healthcare provider can then accurately trim the medical article 700 to fit the patient relying upon the selected hash mark 720. The hash marks 720 can be formed from colored thread woven into the mesh, by printing lines on the mesh after it is knitted, by stamping methods, and/or any other suitable method.

Figure 8:
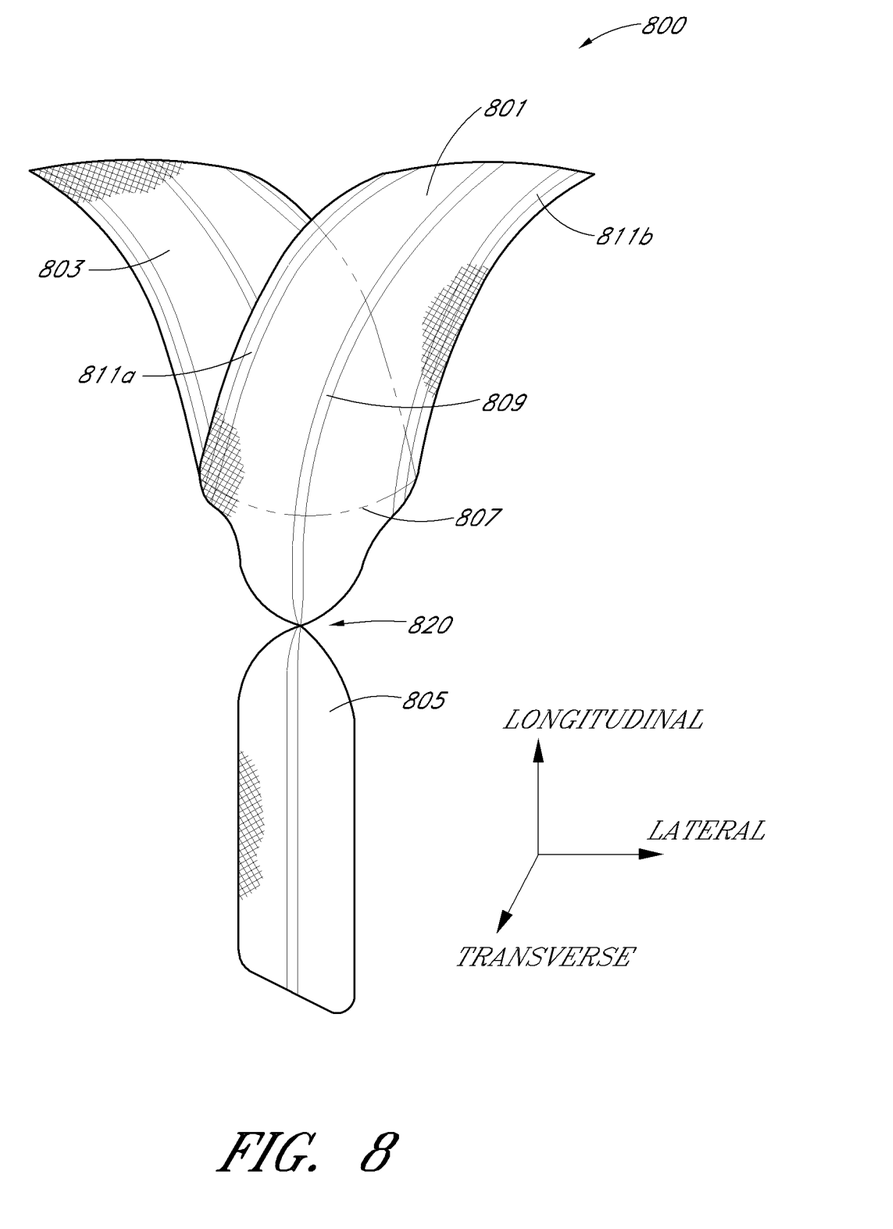
FIG. 8 is a perspective view of another embodiment of an implantable medical article that includes a twist in the sacral flap.

FIG. 8 is a perspective view of an implantable medical article 800 according to yet another embodiment. The implantable medical article 800 includes a sacral flap 805 and two engagement flaps 801, 803 that extend from the sacral flap 805 at an intersection 807 similar to the embodiment described with reference to FIG. 1. Intersection 807 may be generally straight or generally arc shaped as shown in FIG. 8. In the embodiment illustrated in FIG. 8, the sacral flap 805 includes a twist 820 disposed between the distal end of the sacral flap 805 and the intersection 807. The degree of twist or rotation 820 can be selected to rotate the distal end of the sacral flap 805 about an axis through the centerline indicator 809 so as to be generally normal to the surfaces of the engagement flaps 801, 803. The twist 820 can provide a healthcare provider with flexibility in choosing how to secure the engagement flaps 801, 803 to a prolapsed pelvic organ. For example, the twist 820 can allow a healthcare provider to secure the engagement flaps 801, 803 to different walls of a vagina than the walls secured to by the medical article 100 in FIGS. 6A and 6B. In some embodiments, the twist 820 can be releasable and in other embodiments, the sacral flap 805 is permanently twisted. The medical article 800 can also include a centerline indicator 809 and lateral indicators 811a, 811b.

Figure 9:
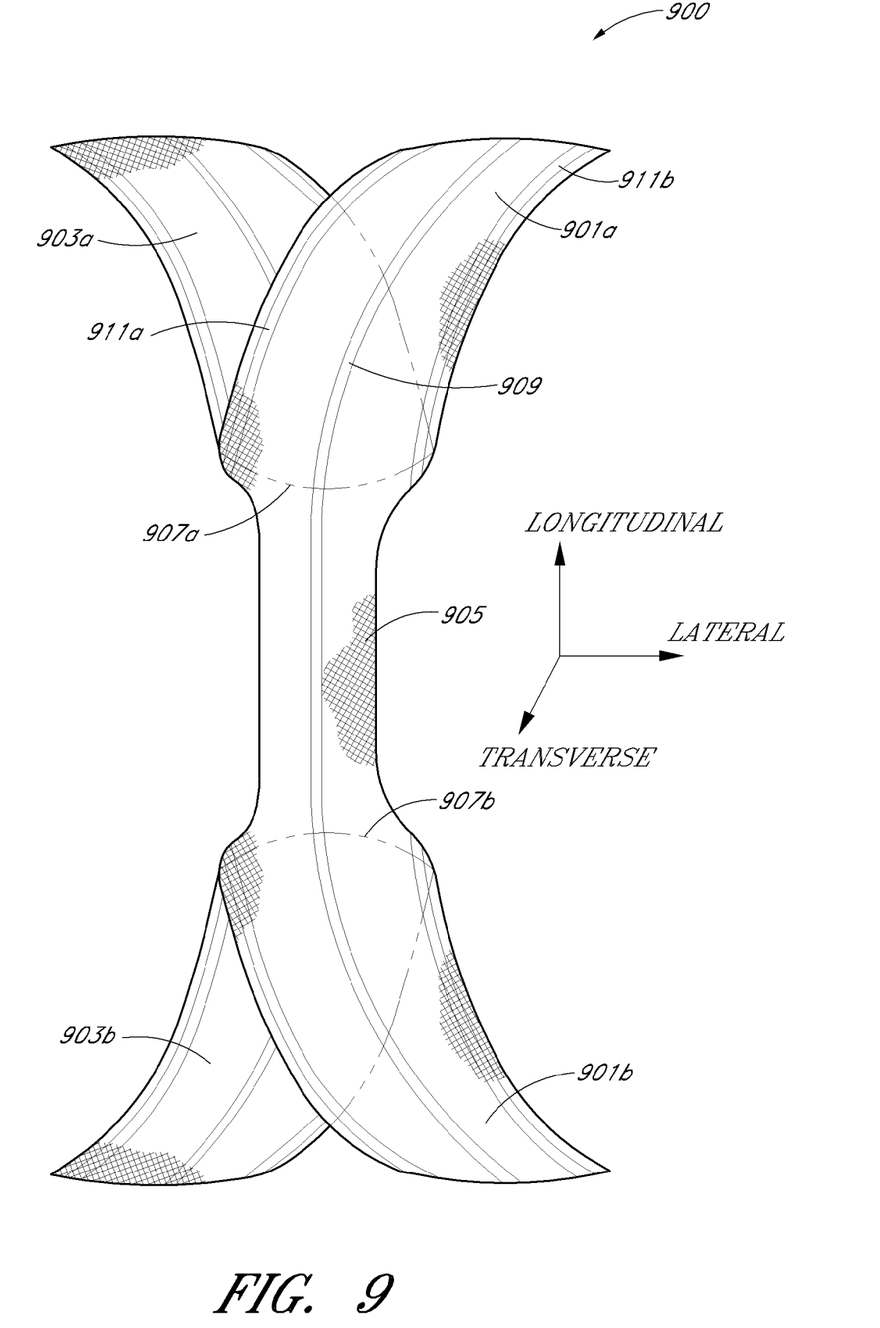
FIG. 9 is a perspective view of an implantable medical article according to another embodiment that has two pairs of engagement flaps and a bridge disposed between the two pairs of engagement flaps.

FIG. 9 is a perspective view of an embodiment of an implantable medical article 900 including a first pair of engagement flaps 901a, 903a, a second pair of engagement flaps 901b, 903b, and a bridge region 905 disposed between the pairs of engagement flaps. The bridge region 905 may have a substantial longitudinal length as illustrated in FIG. 9 or almost no length in the longitudinal direction. Thus, the intersections 907a, 907b may be spaced apart or close together.

The engagement flaps 901, 903 can comprise a single density mesh with the bridge region 905 comprising a dual density mesh. In use, the first pair of engagement flaps 901a, 903a can be secured to a prolapsed pelvic organ, for example, a vagina, and the second pair of engagement flaps 901b, 903b can be secured to another point within the pelvic cavity to suspend the prolapsed organ. In some embodiments, the second pair of engagement flaps 901b, 903b can be used to secure the medical article 900 to a fixed point, for example, the anterior longitudinal ligament overlying a sacral promontory, or to another pelvic organ, for example, the colon. The medical article 900 can also include a centerline indicator 909 and lateral indicators 911a, 911b.

Figure 10:
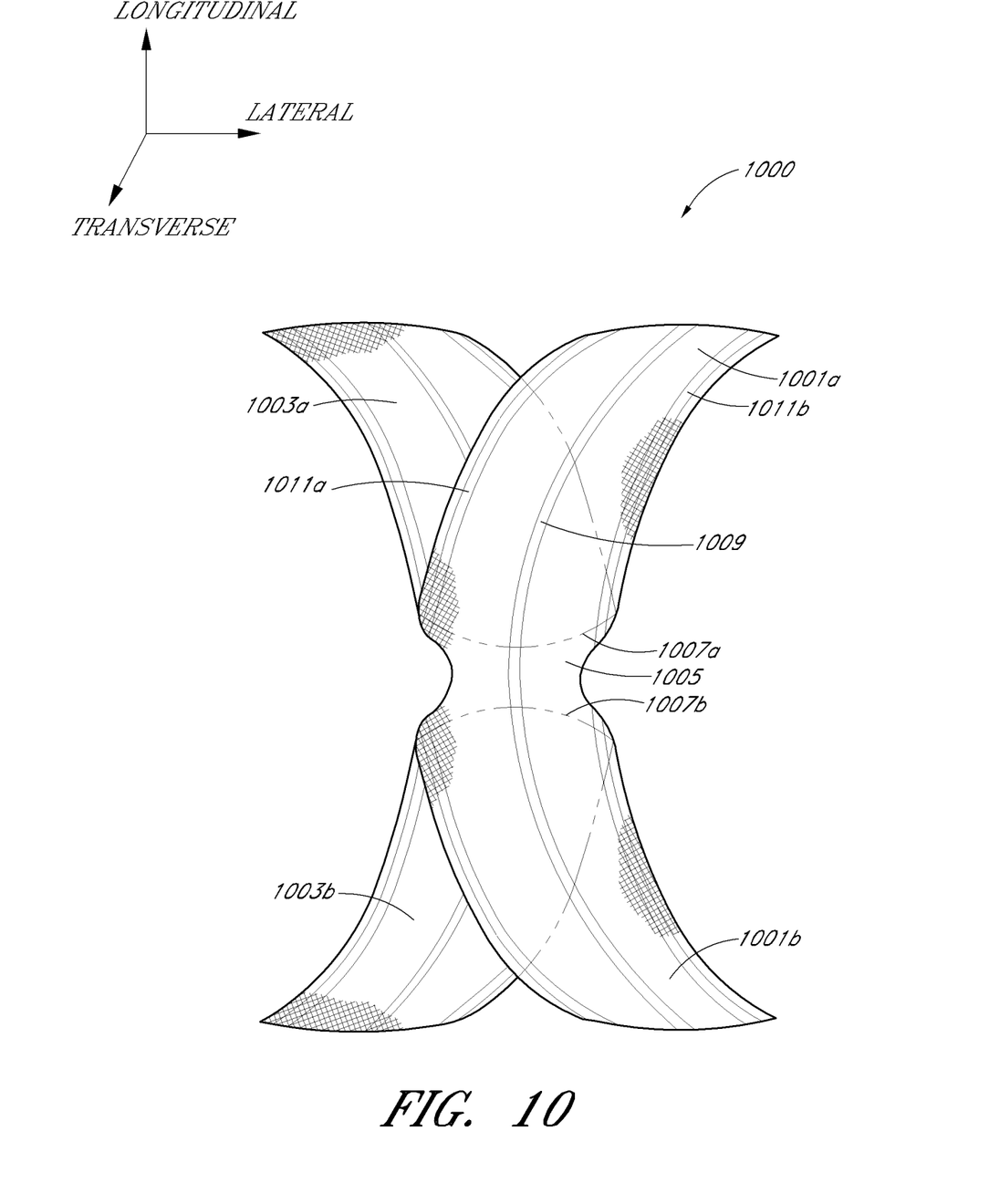
FIG. 10 is a perspective view of an implantable medical article according to another embodiment wherein the bridge disposed between the pairs of engagement flaps is shorter than the bridge shown in FIG. 9.

FIG. 10 shows a perspective view of another embodiment of an implantable medical article 1000 including a first pair of engagement flaps 1001a, 1003a, a second pair of engagement flaps 1001b, 1003b and a bridge region 1005 disposed between the pairs. The bridge region 1005 is shorter than the bridge region 905 shown in FIG. 9. The medical articles shown in FIGS. 9 and 10 can be manufactured using the various knitting methods discussed above. As with the embodiment illustrated in FIG. 9, the medical article 1000 can include a centerline indicator 1009 and lateral indicators 1011a, 1011b.

Figure 11:
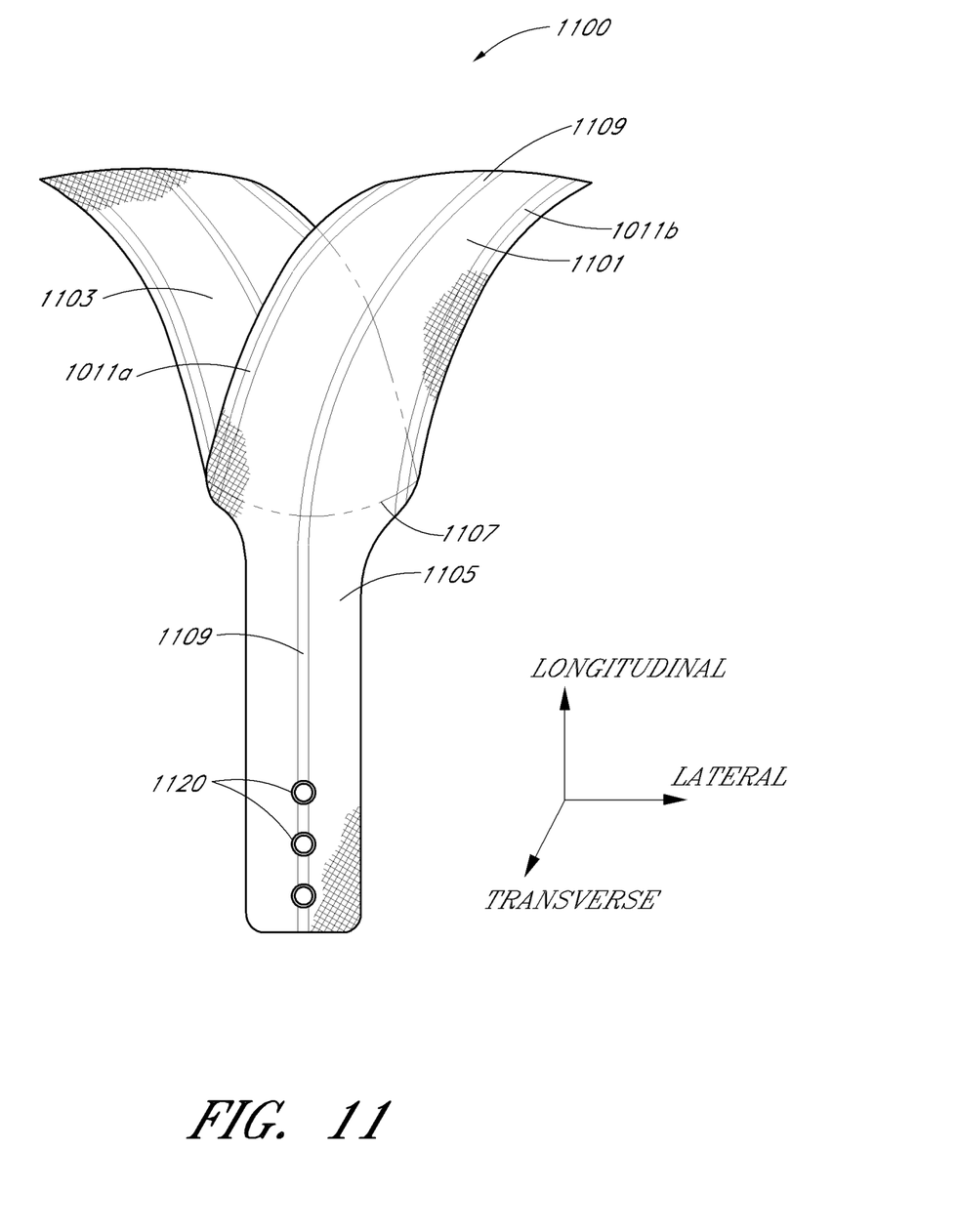
FIG. 11 is a perspective view of another embodiment of an implantable medical article having reinforcement structures in the sacral flap.

FIG. 11 is a perspective view of another embodiment of an implantable medical article 1100 that includes reinforcement structures 1120 formed in the sacral flap 1105. The reinforcement structures 1120 provided additional strength to the sacral flap 1105 at the point(s) where the sacral flap 1105 is attached to a patient. The reinforcement structures 1120 can be configured to inhibit tearing or ripping of the sacral flap 1105 when the sacral flap 1105 is placed in tension. In some embodiments, the reinforcement structures 1120 can comprise grommets. The reinforcement structures 1120 can also be evenly spaced from one another to provide a visual measuring reference for a healthcare provider. In some embodiments, the reinforcement structures 1120 are evenly spaced from one another along the centerline indicator 1109.

Figure 12:
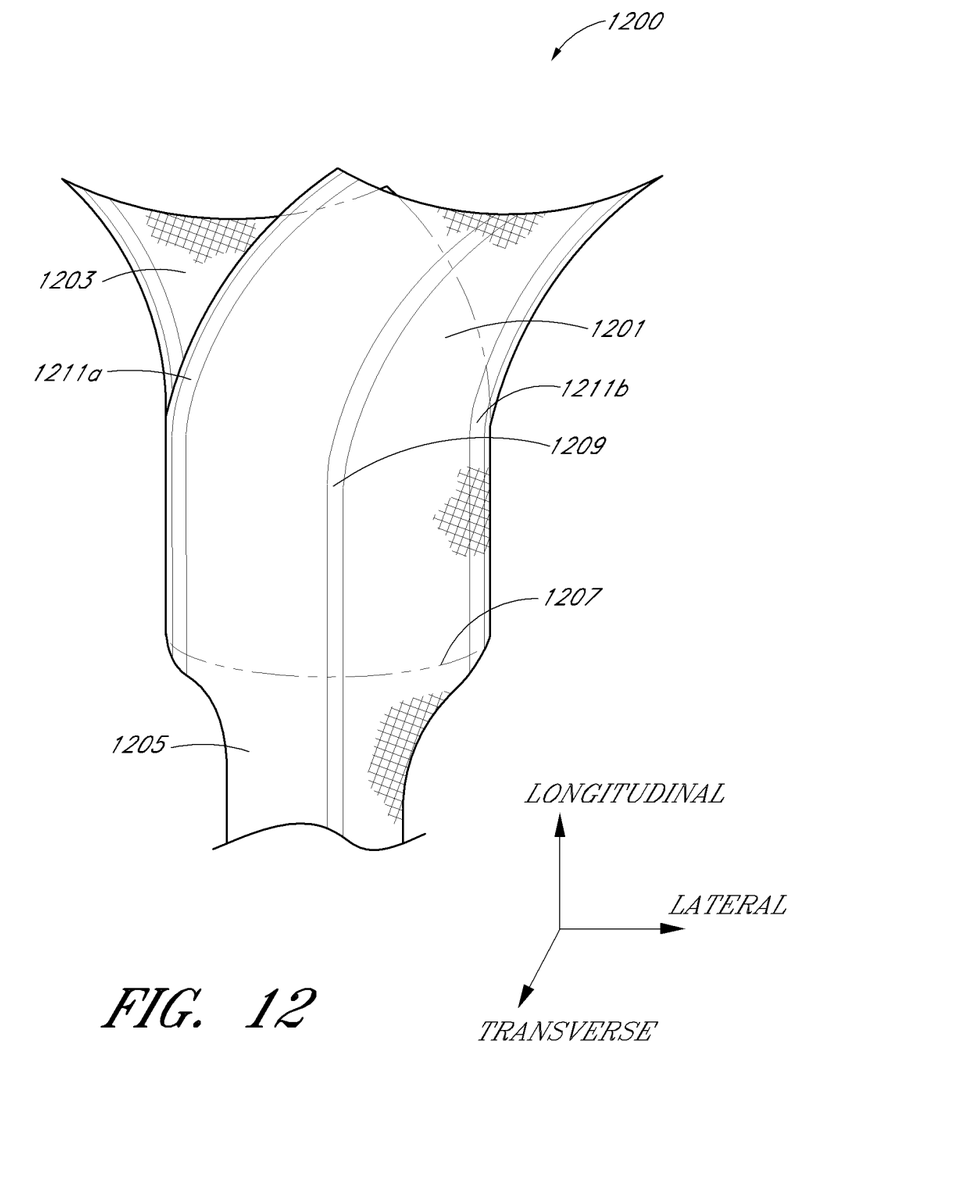
FIG. 12 is a perspective view of an implantable medical article according to another embodiment wherein two engagement flaps form a cup along a portion of the lengths of the engagement flaps.

FIG. 12 is a perspective view of another embodiment of an implantable medical article 1200 that includes a sacral flap 1205 and two pelvic organ engagement flaps 1201, 1203. The sacral flap 1205 and the engagement flaps 1201, 1203 meet at an intersection 1207. The intersection 1207 may be generally straight or generally arc shaped as shown in FIG. 12. The engagement flaps 1201, 1203 may be attached to one another along opposite edges to form a cup or concave shape along at least a portion of the lengths of the engagement flaps 1201, 1203. The cup shape can be configured to receive a portion of a pelvic organ, for example, an apex of a vagina. In some embodiments, the engagement flaps 1201, 1203 may be attached to one another along opposite edges by bonding, stitching, or knitting. The medical article 1200 can also include a centerline indicator 1209 and lateral indicators 1211a, 1211b.

The various embodiments of medical articles and methods of using the same described above provide a number of ways to repair prolapses of various pelvic organs. In addition, the techniques and devices described may be broadly applied for use in a variety of other applications.

Of course, it is to be understood that not necessarily all objects or advantages may be achieved in accordance with any particular embodiment of the invention. Thus, for example, those skilled in the art will recognize that the invention may be embodied or carried out in a mariner that achieves or optimizes one advantage or group of advantages as taught herein without necessarily achieving other objects or advantages as may be taught or suggested herein.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. Accordingly, it should be understood that various features and aspects of the disclosed embodiments can be combined with or substituted for one another in order to form varying modes of the disclosed invention. Thus, it is intended that the scope of the present invention herein disclosed should not be limited by the particular disclosed embodiments described above, but should be determined only by a fair reading of the claims that follow.

What is claimed is:

1. An implantable medical article for use in a procedure to repair a pelvic organ prolapse, the medical article having a length along a longitudinal axis, the medical article comprising:
   a first flap comprising a dual density polymer mesh, the dual density mesh including a first filament and a second filament, the first flap having a first width;
   a second flap comprising a single density polymer mesh, the second flap comprising the first filament, the second flap having a second width; and
   a third flap comprising a single density polymer mesh, the third flap comprising the second filament, the third flap having a third width;
   wherein the first flap, second flap, and third flap are integrally woven together and form an intersection comprising an arc, the intersection including an intersection of the first and second flaps and an intersection of the first and third flaps, and wherein the first filament is integrally and continuously woven across the intersection of the first and second flaps that are in direct physical contact with each other, and wherein the second filament is integrally and continuously woven across the intersection of the first and third flaps that are in direct contact with each other.

2. The medical article of claim 1, wherein the medical article is formed by knitting a uniform piece of mesh.

3. The medical article of claim 1, wherein the medical article is generally y-shaped.

4. The medical article of claim 1, wherein the arc is configured to conform to at least a portion of an apex of a vagina.

5. The medical article of claim 1, wherein the second width is about equal to the third width.

6. The medical article of claim 5, wherein the first width is less than the second width.

7. The medical article of claim 1, wherein the medical article comprises a polypropylene mesh.

8. The medical article of claim 7, wherein the mesh is deformable in a lateral direction.

9. The medical article of claim 8, wherein the mesh is deformable in a longitudinal direction.

10. The medical article of claim 9, wherein the mesh is configured to deform to a greater degree in a lateral direction than in the longitudinal direction.

11. The medical article of claim 1 further comprising a centerline indicator stripe that runs across the length of the medical article in a direction substantially parallel to the longitudinal axis.

12. The medical article of claim 11 further comprising at least two lateral indicator stripes disposed on opposite sides of the centerline indicator stripe, the lateral indicator stripes disposed generally parallel to the centerline indicator stripe.

13. The medical article of claim 1, wherein the first flap comprises a plurality of hash marks, the hash marks disposed generally perpendicular to the longitudinal axis, the hash marks being approximately evenly spaced from one another.

14. An implantable medical article comprising a first flap, a second flap, and a third flap arranged generally in a y-configuration, only two of the flaps having the same material density, wherein a first filament is integrally and continuously woven across an intersection of the first and second flaps that are in direct physical contact with each other, and wherein a second filament is integrally and continuously woven across an intersection of the first and third flaps that are in direct contact with each other.

15. The medical article of claim 14, wherein only one of the flaps has a density that is double a density of another one of the flaps.

16. A method of treating a pelvic organ prolapse of a patient comprising:

providing a y-shaped medical article having at least a first flap, a second flap, and a third flap integrally woven together to form the medical article, the first flap comprising a dual density polymer mesh, the dual density mesh comprising a first filament and a second filament, the second flap comprising a single density polymer mesh, the second flap comprising the first filament, the third flap comprising a single density polymer mesh, the third flap comprising the second filament;

positioning a portion of the medical article over an apex of a vagina of the patient, the portion being defined by an intersection of two of the first, second, and third at least three flaps;

attaching the second flap to a first region of the vagina;

attaching the third flap to a second region of the vagina, the first and second regions being disposed on generally opposite sides of the vagina; and attaching the first flap to an anterior longitudinal ligament overlying a sacral promontory, wherein the first filament is integrally and continuously woven across an intersection of the first and second flaps that are in direct physical contact with each other, and wherein the second filament is integrally and continuously woven across an intersection of the first and third flaps that are in direct contact with each other.

17. The method of claim 16 further comprising measuring a portion of the patient and cutting at least one of the first flap, the second flap, and the third flap based at least in part on the measurement.

* * * * *